US007113818B2

(12) United States Patent
Podoleanu et al.

(10) Patent No.: US 7,113,818 B2
(45) Date of Patent: Sep. 26, 2006

(54) APPARATUS FOR HIGH RESOLUTION IMAGING OF MOVING ORGANS

(75) Inventors: Adrian Podoleanu, Canterbury (GB); John Rogers, Canterbury (GB)

(73) Assignee: OTI Ophthalmic Technologies Inc., Downsview (CA)

( * ) Notice: Subject to any disclaimer, the term of this patent is extended or adjusted under 35 U.S.C. 154(b) by 419 days.

(21) Appl. No.: 10/117,322

(22) Filed: Apr. 8, 2002

(65) Prior Publication Data

US 2003/0199769 A1    Oct. 23, 2003

(51) Int. Cl.
*A61B 6/00* (2006.01)
(52) U.S. Cl. ............... 600/476; 600/425; 600/473; 600/475; 600/477; 600/478
(58) Field of Classification Search ........ 600/425, 600/473, 475–477, 310, 319, 160, 129, 478; 606/1, 2, 4, 11, 15; 607/1, 88–99; 351/206–207, 351/211–212, 221, 246; 356/654, 146, 349, 356/357
See application file for complete search history.

(56) References Cited

U.S. PATENT DOCUMENTS

| 4,373,787 A | | 2/1983 | Crane et al. | |
|---|---|---|---|---|
| 4,817,623 A | * | 4/1989 | Stoddart et al. | ............ 600/477 |
| 4,994,744 A | * | 2/1991 | Glover et al. | ................ 324/309 |
| 5,321,501 A | | 6/1994 | Swanson et al. | |
| 5,459,570 A | | 10/1995 | Swanson et al. | |
| 5,469,261 A | | 11/1995 | Hellmuth et al. | |
| 5,491,524 A | * | 2/1996 | Hellmuth et al. | ........... 351/212 |
| 5,493,109 A | | 2/1996 | Wei et al. | |
| 5,537,162 A | | 7/1996 | Hellmuth et al. | |
| 5,611,342 A | * | 3/1997 | Widder | ....................... 600/431 |
| 5,973,781 A | | 10/1999 | Moeller et al. | |
| 5,975,697 A | * | 11/1999 | Podoleanu et al. | ......... 351/206 |
| 5,991,697 A | * | 11/1999 | Nelson et al. | ................ 702/49 |
| 6,137,585 A | | 10/2000 | Hitzenberger et al. | |
| 6,201,989 B1 | * | 3/2001 | Whitehead et al. | ......... 600/476 |

(Continued)

FOREIGN PATENT DOCUMENTS

WO    WO 90/00028    1/1990

(Continued)

OTHER PUBLICATIONS

"Optical coherence tomography" by Huang et al., Science 254, (1991), pp. 1178.

(Continued)

*Primary Examiner*—Brian L. Casler
*Assistant Examiner*—Baisakhi Roy
(74) *Attorney, Agent, or Firm*—Marks & Clerk; Richard J. Mitchell

(57) ABSTRACT

Apparatus for high resolution imaging of a moving object comprises a source of low coherence light, an optical coherence tomography imaging instrument or a dual channel, optical coherence tomography/confocal imaging instrument, a transverse scanner, an interferometer, depth adjustment means, and interface optics. First and an optional second sensing blocks sense the axial and respectively the transverse position of the object. A splitting element is shared so that the interface optics and the sensing blocks have a common axis of light transmitted to and from the object. Timing means establishes a timing, and timing intervals and reference times for images as they are taken. The acceptability of each scanned image is determined according to predetermined criteria. A series of en-face OCT images, or of longitudinal OCT images of the object may be taken at different depths or transverse coordinates, and the stack of collected images is used to build 3D profiles of the object.

42 Claims, 11 Drawing Sheets

U.S. PATENT DOCUMENTS

| | | | |
|---|---|---|---|
| 6,220,706 B1* | 4/2001 | Foley | 351/209 |
| 6,485,413 B1* | 11/2002 | Boppart et al. | 600/160 |
| 6,546,272 B1* | 4/2003 | MacKinnon et al. | 600/407 |
| 6,769,769 B1* | 8/2004 | Podoleanu et al. | 351/221 |
| 2003/0045798 A1* | 3/2003 | Hular et al. | 600/476 |
| 2004/0144925 A1* | 7/2004 | Stoddart et al. | 250/363.04 |

FOREIGN PATENT DOCUMENTS

| | | |
|---|---|---|
| WO | WO 01/24688 | 11/2001 |

OTHER PUBLICATIONS

"Optical coherence tomography" by A. F. Fercher, in J. Biomed. Opt., 1(2), (1996), pp. 157-173.

"Coherence Imaging by Use of a Newton Rings Sampling Function" by A. Gh. Podoleanu, G. M. Dobre, D. J. Webb, D. A. Jackson, published in Opt. Lett., vol. 21, No. 21, (1996), pp. 1789-1791.

"En-face Coherence Imaging Using Galvanometer Scanner Modulation" by A. Gh. Podoleanu, G. M. Dobre, D. A. Jackson, Opt. Lett. 23, pp. 147-149, 1998.

"Transversal and Longitudinal Images from the Retina of the Living Eye Using Low Coherence Reflectometry", by Podoleanu et al., published in the Journal of Biomedical Optics, (1998), 3(1), pp. 12-20. 1998.

"Measurement of the thickness of fundus layers by partial coherence tomography", published by Drexler et al., in Optical Engineering, vol. 34, No. 3, (1995), pp. 701-771.

* cited by examiner

APPARATUS FOR HIGH RESOLUTION IMAGING OF MOVING ORGANS

FIELD OF THE INVENTION

The present invention relates to an optical coherence tomographic apparatus which can be used to provide images from moving objects such as human organs, with low sensitivity to the axial and transverse movements of the objects being scanned.

The description which follows refers mainly to the eye as the object. However, this will be understood as merely exemplary, and not as a restriction of the application of the present invention. Where "eye" is mentioned, a more general transparent and scattering object or organ may be considered as well to be the scanned object.

DESCRIPTION OF THE PRIOR ART

High depth resolution imaging of the eye fundus can be achieved by optical coherence tomography (OCT) as shown in the paper "Optical coherence tomography" by D. Huang, E. A. Swanson, C. P. Lin, J. S. Schuman, W. G. Stinson, W. Chang, M. R. Hee, T. Flotte, K. Gregory, C. A. Puliafito and J. G. Fujimoto, *Science* 254, (1991). pp. 1178 and in the paper "Optical coherence tomography" by A. F. Fercher, in *J. Biomed. Opt.*, 1(2) (1996), pp. 157–173. OCT has the potential of achieving much better depth resolution, as the limit in this case is not set by the eye, but by the coherence length of the source. (Superluminiscent diodes and mode-locked lasers are now available with coherence lengths less than 20 :m and 5 µm respectively).

An OCT is now commercially available, which produces longitudinal images only, i.e. images in the planes (x,z) or (y,z), where the z axis is perpendicular to the patient's face and x and y axes are in the plane of the patient's face. Examples of such apparatus for longitudinal imaging are described in U.S. Pat. Nos. 5,493,109, 5,537,162, 5,491,524, 5,469,261, 5,321,501 and 5,459,570.

OCT has also been reported as capable of providing en-face (or transverse) images, as reported in "Coherence Imaging by Use of a Newton Rings Sampling Function" by A. Gh. Podoleanu, G. M. Dobre, D. J. Webb, D. A. Jackson, published in *Opt. Lett.*, Vol. 21, No. 21, (1996), pp. 1789–1791 and "En-face Coherence Imaging Using Galvanometer Scanner Modulation" by A. Gh. Podoleanu, G. M. Dobre, D. A. Jackson, *Opt. Lett.* 23, pp. 147–149, 1998. When applied to the eye, the en-face OCT images look fragmented, as demonstrated in "Transversal and Longitudinal Images from the Retina of the Living Eye Using Low Coherence Reflectometry", by A. Gh. Podoleanu, Mauritius Seeger, George M. Dobre, David J. Webb, David A. Jackson and F. Fitzke, published in the *Journal of Biomedical Optics*, (1998), 3(1), pp. 12–20, 1998. An example of such apparatus for transverse imaging is described in U.S. Pat. No. 5,975,697. These papers also demonstrate that, owing to the low coherence length, the OCT transversal images show only fragments of the retina and are difficult to interpret. In addition, due to the curvature of the retina at the back of the eye lens and due to the angular path variation of the scanned ray, the OCT transversal images show arcs at the extremities of the field investigated when the angular scanned field is larger than, say 6°. For example, for an eye lens of 2 cm focal length, the coherence plane curves in the form of an arc where at maximum angular deviation, of +/−3°, the distance from the plane is larger than 70 µm, which is much higher than the coherence length of the most super luminescent diodes on the market.

To improve the usefulness of en-face OCT images, a dual presentation of images was proposed as described in U.S. Pat. No. 5,975,697. Two en-face images are produced and displayed simultaneously, one OCT and the other confocal, similar to the image produced by a scanning laser ophthalmoscope (SLO). The dual presentation allows the fragments sampled by the OCT from the fundus to be uniquely placed in correspondence with fundus images displayed by the confocal channel. The confocal channel has a much larger depth resolution and the images look continuous, offering good guidance of the part of the eye investigated. The dual display is essential for guidance and subsequent alignment of the stack of en-face images prior to construction of the 3D volume investigated.

However, due to the inadvertent axial movement of the eye during investigation, the absolute depth of the individual images in the stack loses precision. The confocal image is useful in aligning the stack transversally, but has no bearing on the axial position of the eye.

Different methods have been suggested for reducing the influence of eye movements.

A method suggested to be used for the eye, presented in the paper "Measurement of the thickness of fundus layers by partial coherence tomography", published by Drexler W., Sattman H., Hitzenberger, Ch. K, Fercher, A. F. in *Optical Engineering*, vol. 34, No. 3, (1995), pp. 701–71 and also described in U.S. Pat. No. 6,137,585, uses a tandem interferometer tuned on the path imbalance between the cornea and the retina. The signals reflected from the cornea and from the retina are allowed to interfere. In order to achieve axial movement free interference, a two beam interferometer is used either in the incident path to the eye or in the return path from the eye. The distance retina—cornea is obtained by matching the interferometer optical path difference (OPD) with the OPD associated with the eye length. Using the cornea as reference has the following disadvantages: (i) The tear film reflectivity is 2% from the reflectivity of a good mirror. This results in a proportionately lower strength for the OCT signal than when using a mirror. (ii) The cornea and retina are multiple layer surfaces, and the tandem interferometer method produces a mix of peaks in the interferogram. It is practically impossible to establish the correspondence of these peaks to layers in the cornea and retina. For instance, the ratio of reflections from the anterior and posterior cornea is less than 1/10. This means that an OCT equipped with a logarithmic amplifier will show replicated OCT images of the retina due to the anterior as well as due to the posterior cornea; (iii) The magnitude of the reference signal originating by reflection from the cornea strongly depends on the eye position. (iv) The main disadvantage of the method lies in the poor signal to noise ratio, as both interfering signals come from the target and have relatively low amplitudes. To collect similar intensity signals, a diffracting focusing element was introduced in the object beam, as described in U.S. Pat. No. 5,973,781. This enhances the collection of light from the cornea when a collimated beam is directed to the eye. This complicates the set-up and reduces the S/N ratio even further.

In order to eliminate the eye movements, eye tracking is also possible. U.S. Pat. No. 4,373,787 uses the first and fourth Purkinje reflections to generate output signals indicative of eye rotation and translation. The fourth Purkinje reflection is weak, as it comes from the posterior surface of the lens and as another disadvantage, such eye trackers are not sensitive to the axial eye movements.

Pairs of an emitter and a quadrant receiver mounted off axis of the eye can be used to detect transverse as well as axial eye movements, as described in U.S. Pat. No. 6,220,706. Alternatively, two camera off-axis eye trackers have been suggested, such as in WO patent 01/24688 A1, mainly to infer the lateral eye movement with the possibility to sense the axial movement by processing differentially the signals from the two cameras. However, all these solutions require extra devices and the measuring error may not be at the level required by the high resolution imaging instrument.

Patent WO 90/00028 describes another solution, where a reflector is mounted on the eye and reflection thereof are indicative of rotational movement of the eye. Apart from being insensitive to the axial movement, the attachment of tiny reflectors to the eye is not applicable to all eyes and the reflector requires sterilisation or to be devised as for single usage.

Thus, a need exists for low cost procedures to detect and measure the axial and transverse movements of the organs being scanned, with high precision without introducing artifacts in the image nor reducing its quality and to apply these results into the real time imaging process.

OBJECTS OF THE INVENTION

The present invention sets out to solve the above problems and relates to methods and apparatuses to sense the organ position while acquiring stacks of OCT images and then of using the position of the organ to correctly reproduce the 3D volume of the part of the organ imaged. The method and apparatuses subject of the proposal use a minimum of extra components for the sensing of the axial movement of the organ and employ the very imaging instrument to measure the transverse movement of the organ.

Thus, the present invention provides a method and apparatus to sense the actual depth position of each individual en-face OCT image collected in a stack at different set depth positions and use the actual values of the depth position to: (i) validate the image, (ii) reorder in depth the images in the stack prior to 3D representation; (iii) trigger acquisition of new en-face OCT images to cover those depth positions which due to organ movement, have either not been sampled or discarded by the processing method.

More preferably, the confocal image collected by the confocal channel of a dual OCT/confocal imaging apparatus is used to validate each OCT en-face image in the very process of its acquisition.

Further, the present invention provides a method and apparatus to sense the instantaneous depth position of the organ while a stack of longitudinal OCT images is acquired at different set transverse coordinate positions, and use the actual values of the depth position to: (i) validate the image, (ii) align the longitudinal OCT images in the stack prior to 3D representation and (iii) trigger acquisition of new longitudinal OCT images from those transverse positions which due to organ movement have been discarded by the processing method.

Likewise, the confocal image collected by the confocal channel of a dual OCT/confocal imaging apparatus, is used to validate each longitudinal OCT image in the very process of its acquisition.

Still further, the present invention provides a method and apparatus to sense the transverse movement of the organ using supplementary transverse position devices.

SUMMARY OF THE INVENTION

To that end, the present invention provides an apparatus for high resolution imaging of a moving object located at an object location, which comprises: a source of low coherence light; an optical coherence tomography imaging system for scanning an object to be scanned, where the imaging system is chosen from the group consisting of an optical coherence tomography imaging instrument and a dual channel optical coherence tomography/confocal imaging instrument.

There is a transverse scanning means to effect transverse scanning of the beam; an interferometer in the respective optical coherence tomography imaging instrument; depth adjustment means comprising electronically controllable optical path altering means for altering the optical path difference in the interferometer; and interface optics for transferring an optical beam from the respective transverse scanning means of the optical coherence tomography imaging system to the object located at the object location, and for transferring an optical output beam reflected and scattered from the object back to the optical coherence tomography imaging system and to the confocal receiver in the dual channel optical coherence tomography/confocal imaging instrument.

There is a first sensing block for sensing the axial position of the object, and optionally a second sensing block for sensing the transverse position of the object.

There is also a splitting element shared by the sensing block, whereby the interface optics and the sensing block have a common axis of the light being transmitted to and from the object.

There is a timing means for establishing a timing reference for taking a series of images of the object, and for establishing timing intervals and reference times for the images as they are taken.

There are processing means for determining the acceptability of each scanned image according to predetermined criteria.

Thus, a series of en-face images of the object at different depths are taken, by altering the optical path difference in the interferometer.

An alternative, second, principal embodiment of the present invention is much the same as that described above, except that it employs first and second sensing blocks for sensing the axial position of the object and the transverse position of the object, respectively.

In this alternative embodiment of the present invention, the splitting element is shared by both the first sensing block and the second sensing block, so that the interface optics and the first and second sensing blocks have a common axis of the light being transmitted towards and from the object.

Thus, a series of longitudinal optical coherence tomography images are taken for different values of a rectangular transverse coordinate along an axis orthogonal to the transverse scanning axis used for scanning the series of longitudinal images.

In the first embodiment, the series of en-face images are obtained in a manner chosen from the group consisting of continuously, and in a stepwise manner. Likewise, in the second embodiment, a series of longitudinal optical coherence tomography images are obtained in a manner chosen from the group consisting of continuously, and in a stepwise manner.

In any embodiment of the present invention, the splitting element may pass all of the light from the interface optics to the object, and back; and off-axis beams for sensing the axial or transverse position, respectively, are employed by the respective first and second sensing blocks.

Either of the first sensing block or the second sensing block may employ pairs of emitters and photoreceivers configured so as to provide axial or transverse coordinate position information for the object.

In any embodiment of the present invention, the splitting element may be a beam splitter.

If so, the beam splitter may be chosen from the group consisting of cold mirrors, hot mirrors, and edge filters. Thus, separate wavelength bands are allowed to be transmitted and reflected.

Moreover, one of two separate wavelength bands may be allocated to the optical imaging system, and the other of the two separate wavelength bands may be allocated to either the at least first sensing block or the second sensing block.

Either of the first sensing block or the second sensing block may be an independent low coherence interferometer, or it may be a frequency modulation continuous wave device.

In either of the two principal embodiments of the present invention, a grid of N depth positions is defined by dividing the range of the depth to be scanned, or the range of the transverse coordinate to be scanned, by N, and assigning the respective N depth positions accordingly.

Then, a respective depth position or transverse coordinate position for each acquired image is compared with its respective real axial position or its respective real transverse position as determined by the respective first sensing block or second sensing block.

Thus, for each scanned image, a calculated axial position, or a calculated transverse coordinate position, is allocated in keeping with the comparison of the real axial position or the real transverse coordinate position, with the grid.

Thereafter, a determination is made after a set of images has been acquired as to whether any of the N depth intervals or whether any of the N transverse coordinate intervals has not been sampled, or has been oversampled.

Then, a scanning procedure is repeated until each of the N depth intervals or each of the N transverse coordinate intervals on the grid has been sampled at least once.

Also, the calculated axial position or the calculated transverse coordinate position for each slice of a set of images may be an average value determined from the axial positions measured by the at least first sensing block or an average value determined from the transverse coordinate positions measured by the second sensing block, during the acquisition of that slice.

Each such calculated axial position or each such calculated transverse coordinate position is valid or determined only when all axial positions measured by first sensing block, or only when all transverse coordinate positions measured by the second sensing block, are less than a respective predetermined threshold axial error, or are less than a predetermined threshold transverse coordinate error.

In the first principal embodiment of the present invention, the calculated axial position for each slice is the value from grid of depth values closest to an average depth as determined by the first sensing block during the acquisition of that slice.

Likewise, in the second principal embodiment of the present invention, the calculated transverse coordinate position for each slice is the value from the grid of transverse coordinate values closest to an average transverse coordinate as determined by the second sensing block during the acquisition of that slice.

In either event, each such calculated axial position, or each such calculated transverse coordinate position, is valid or determined only when all axial positions or all transverse coordinate positions, as measured by the respective first sensing block or second sensing block, are less than a respective predetermined threshold axial error or a predetermined threshold transverse coordinate error.

Moreover, whenever more than one image per depth interval or per transverse coordinate interval is collected, the image having a calculated axial position or a calculated transverse coordinate position which is closest to the respective grid value, is the one which is chosen.

In any embodiment of the present invention, after a set of images has been acquired and a determination is made as to which of the N depth intervals or which of the N transverse coordinate intervals has not yet been sampled, new slices are collected for each of the depth intervals or for each of the transverse coordinate intervals that has not yet been sampled, until each of the N depth intervals or each of the N transverse coordinate intervals on the respective grid has been sampled at least once.

Thus, after a stack of N images with at least one image for each of the N depth intervals or each of the N transverse coordinate intervals has been acquired, then a 3D reconstruction of the object can be made.

Still further, after at least one image for each of the N depth intervals or each of the transverse coordinate intervals has been acquired, where there are P images for any specific depth interval, or for any specific transverse interval; then each image for each respective depth interval, or for each respective transverse coordinate interval, is assigned a weight of 1/P. Then after a stack of N images with at least one image for each of the N depth intervals, or for each of the N transverse coordinate intervals, has been acquired, a 3D reconstruction of object can be made.

In the first principal embodiment of the present invention, a dual channel optical coherence tomography/confocal imaging instrument may be employed.

For either principal embodiment, a predetermined axial threshold error value will be established.

Also, for the second principal embodiment of the present invention, a predetermined transverse threshold error value will be established.

Typically, in either principal embodiment, each slice for each depth interval is validated for axial shifts less than the predetermined axial threshold error value.

Also, in either principal embodiment each slice may also be validated for transverse shifts less than the predetermined transverse threshold error value.

However, when a depth interval shift as measured by the first sensing block during the slice acquisition is greater than the predetermined axial threshold error value, then the scanned slice is discarded and the corresponding depth value is determined not to have been sampled.

Likewise, in the second principal embodiment of the present invention, if a transverse interval shift as measured by the second sensing block during the slice acquisition is greater than the predetermined transverse threshold error value, then the scanned slice is discarded and the corresponding depth value is determined not to have been sampled.

In either case, the sampling continues until at least one slice has been acquired for each one of the N depth intervals.

The second principal embodiment of the present invention may also employ a dual channel optical coherence tomography/confocal imaging instrument.

As before, a predetermined transverse threshold error value will be established.

Each slice is validated for transverse shifts along the transverse scanning direction less than the transverse threshold error value.

When at least one of the transverse interval shift along any transverse scanning direction as measured by the second sensing block, or a transverse interval shift along the transverse scanning direction as measured from the image of the confocal receiver after the slice was acquired by comparing the transverse shift of lines along depth in relation to a line at a first depth coordinate interval, or in relation to a reference line in the image at a reference depth interval, is greater than the transverse threshold error value, then the scanned slice is discarded and the corresponding transverse coordinate value is determined not to have been sampled.

In that case, once again the sampling continues until at least one slice has been acquired for each one of said N transverse coordinate intervals.

Another approach taken with respect to the second principal embodiment is that a longitudinal optical coherence tomography slice is acquired for each one of a grid of N equidistant transverse coordinate positions that are within the transverse coordinate range.

In that case, the calculated transverse position for each one of the N transverse coordinate positions is an average value determined from the transverse coordinate positions measured by the second sensing block during the acquisition of that slice Thus, each such calculated transverse coordinate position is valid or determined only when all transverse coordinate positions measured by the second sensing block are less than a predetermined threshold transverse coordinate error.

For each scanned slice referred to immediately above, a calculated transverse position is allocated in keeping with a comparison of the respective real transverse position as determined by the second sensing block.

Then, a determination is made after a set of slices has been acquired as to whether any of the N transverse coordinate positions has not been sampled or has been oversampled; following which a scanning procedure is repeated until each of the N transverse coordinate positions on said grid has been sampled at least once.

In this latter embodiment, the calculated transverse coordinate position for each slice is the value from the grid of transverse coordinate values closest to an average transverse coordinate as determined by the second sensing block during the acquisition of that slice.

Each such calculated transverse coordinate position is valid or determined only when all transverse coordinate positions measured by the second sensing block are less than a predetermined threshold transverse coordinate error.

For more than one image per transverse coordinate interval collected, the image having a calculated transverse coordinate position which is closest to the respective grid value is the one which is chosen.

According to this latter embodiment, after a set of images has been acquired and a determination is made as to which of the N depth intervals has not been sampled, new slices are collected for each of the transverse coordinate intervals not yet sampled until each of the N transverse coordinate intervals on said grid has been sampled at least once.

Then, after a stack of N images with at least one image for each of said N transverse coordinate intervals has been acquired, a 3D reconstruction of said object is made.

In yet another variation of the second principal embodiment of the present invention, once again a dual channel optical coherence tomography/confocal imaging instrument is employed. As before, both of a predetermined axial threshold error value and a predetermined transverse threshold error value are established.

Each slice for each depth interval is validated for axial shift less than the axial threshold error value, and is also validated for transverse shifts along any rectangular transverse direction less than the transverse threshold error value.

Then, when at least one of a depth interval shift as measured by the first sensing block during the acquisition of the slice, and a transverse interval shift along any rectangular transverse direction as measured by the second sensing block during acquisition of the slice, is greater than the respective predetermined axial threshold error value or the predetermined transverse threshold error value, then the scanned slice is discarded and the corresponding transverse coordinate value is determined not to have been sampled.

As before, the sampling continues until at least one slice has been acquired for each one of said N transverse coordinate intervals.

Still another variation of the second principal embodiment of the present invention also employs a dual channel optical coherence tomography/confocal imaging instrument. Once again, a predetermined axial threshold error value and a predetermined transverse threshold error value are established.

However, in this case, each slice for each depth interval is validated for axial shift less than the axial threshold error value and is also validated for transverse shifts along rectangular transverse directions less than the transverse threshold error value.

When at least one of a depth interval shift as measured by the first sensing block during the acquisition of the slice, and a transverse interval shift along a rectangular transverse direction to the transverse scanning in the longitudinal OCT image, as measured by the second sensing block during acquisition of the slice, is greater than the respective predetermined axial threshold error value and the predetermined transverse error threshold value; or when a transverse interval shift along the transverse scanning direction as measured from the image of the confocal receiver after the slice was acquired by comparing the transverse shift of lines along depth in the OCT channel in relation to a line at a first depth coordinate interval, or in relation to a reference line in the image at a reference depth interval, is greater than the predetermined transverse error threshold value; then the scanned slice is discarded and the corresponding transverse coordinate value is determined not to have been sampled.

Again, the sampling continues until at least one slice has been acquired for each one of said N transverse coordinate intervals.

In any embodiment of the present invention, a predetermined threshold axial error may be established, and it may be adjustable as a trade-off between axial resolution and acquisition time.

Also, in any embodiment of the present invention, a predetermined threshold transverse coordinate error may be established, and it may also be adjustable as a trade-off between transverse coordinate resolution and acquisition time.

In any embodiment of the present invention, typically the sensing rate of either of the first sensing block or the second sensing block, will be at least 10 times greater than the rate at which scanned images are acquired.

In apparatus according to the first principal embodiment of the present invention, an optical coherence tomography imaging instrument may be employed.

In that case, a predetermined axial threshold error value will be established.

Then, each slice for each depth interval will be validated for an axial shift less than the axial threshold error value.

However, when a depth interval shift as measured by the first sensing block during the acquisition of the slice is greater than the predetermined axial threshold error value, the scanned slice is discarded and the corresponding transverse coordinate value is determined not to have been sampled.

As before, the sampling will continue until at least one slice has been acquired for each one of N transverse coordinate intervals.

Also, in apparatus according to the second principal embodiment of the present invention, a dual channel optical coherence tomography/confocal imaging instrument may be employed; and each of a predetermined axial threshold error value and a predetermined transverse threshold error value may be established.

In this case, each slice for each depth interval is validated for an axial shift less than the axial threshold error value, and is also validated for transverse shifts along the rectangular transverse direction to the transverse scanning in the longitudinal OCT image less than the transverse threshold error value.

When at least one of a depth interval shift as measured by the first sensing block during the acquisition of the slice, and the transverse interval shift along the transverse scanning direction in the longitudinal OCT image, as measured from the image of the confocal receiver after the slice was acquired by comparing the transverse shift of lines along depth in the OCT channel in relation to a line at a first depth coordinate interval, or in relation to a reference line in the image at a reference depth interval, is greater than the respective predetermined axial threshold error value or the predetermined transverse error threshold value, then the scanned slice is discarded and the corresponding transverse coordinate value is determined not to have been sampled.

The sampling will continue until at least one slice has been acquired for each one of said N transverse coordinate intervals.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following discussion.

Figure 1:
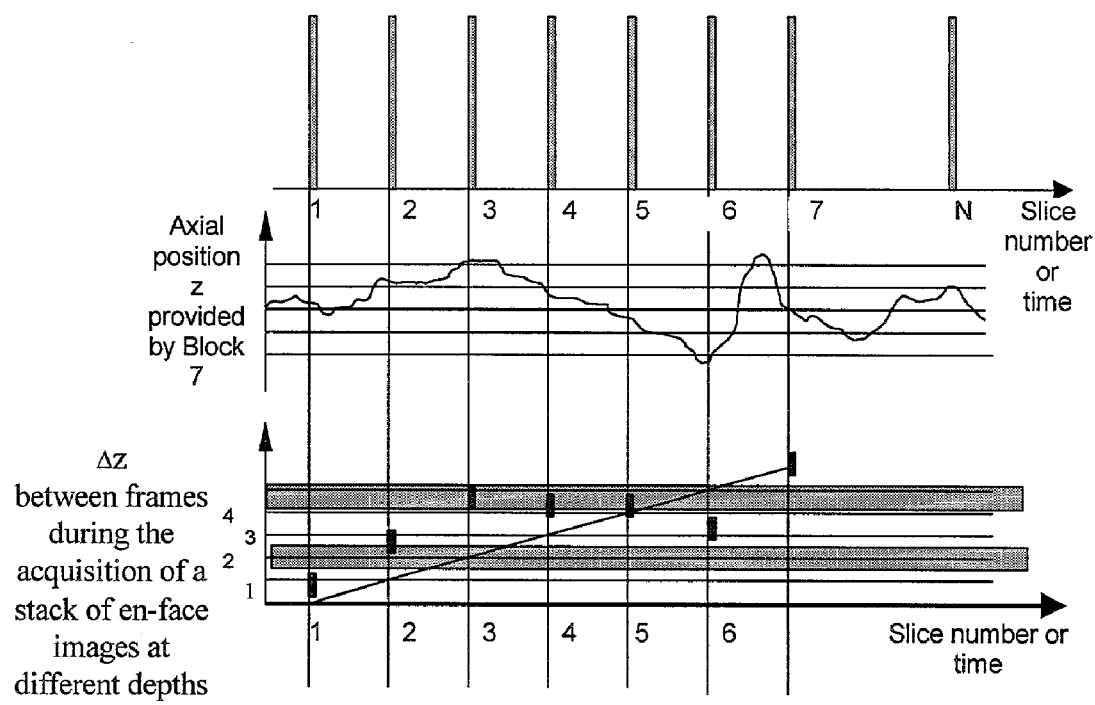
FIG. 1 is an example of a real life situation where the depth of the slices collected during the acquisition of en-face OCT images does not correspond to the time inferred from the instantaneous position of the translation stage in the OCT channel, due to the organ movement.

FIG. 1 shows the effect of axial movements of the organ on the sampling of the stack of en-face OCT images. The line shows the imposed depth variation versus time, set by the device in the OCT channel which alters the optical path difference. If the object does not move, the depth position varies linearly with time and the depth interval between frames is constant, δz. Several situations are possible:

Correct slicing, when the optical path and axial position can be inferred from the time coordinate. For instance, the slices collected at moments 1 and 5 correspond to the expected depth at the depth intervals 1 and 5;

Slices at moments, n, do not correspond to the expected depth interval positions, n. For instance, the slice at the moment 2 is collected from the depth interval 3 and the slice at the moment 6 is collected from the depth interval 4;

Over-sampling, when the organ moves at the same rate and in the same direction with the depth change in the OCT channel. For instance, the depth 5 is oversampled by slices at the moments 3, 4 and 5; and No-sampling, when the eye jumps axially faster than the depth change rate, and as a consequence, some depth intervals are not sampled at all. For instance, no slice has been collected from the depth interval 2.

The 3D volume can also be reproduced by collecting longitudinal OCT images, (x,z) at different y positions, or longitudinal OCT images (y,z) at different x positions, or longitudinal OCT images, (θ,z) at different ρ positions for angles θ around a fixed point describing circles of radius ρ. The coordinate y, x or ρ in each of these cases respectively is denoted as the rectangular transverse coordinate. While collecting longitudinal OCT images, axial movements of the object result in the whole image being moved forward or back.

Figure 2:
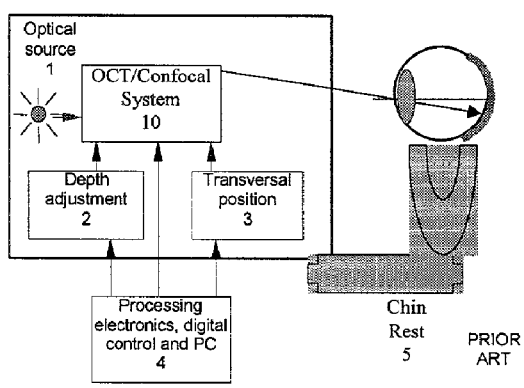
FIG. 2 is prior art and shows, in diagrammatic form, the main elements of a high resolution ophthalmic apparatus, using OCT or OCT/confocal dual channel imaging apparatus.

FIG. 2 shows, in diagrammatic form, the main elements of a high resolution ophthalmic apparatus, using OCT. The core of the apparatus is an OCT imaging system 10, which may or may not incorporate a confocal dual channel, of the type explained in the U.S. Pat. No. 5,975,697, illuminated by a low coherence source, 1, which may or may not be of adjustable coherence (as explained in the same U.S. Pat. No. 5,975,697). In order to explore the depth, the apparatus is equipped with means, 2, to alter the optical path difference in the interferometer of the OCT channel, and means, 3, for transversally scanning the optical ray over the object, 20, both blocks 2 and 3 are under the control of the processing electronic block, 4 which may incorporate a PC. When the apparatus is used to image the eye of a patient, a chin rest, 5, is used to support some blocks of the apparatus and the patient head.

3D complete information could be collected in different ways, either acquiring many longitudinal OCT images at different en-face positions (i.e. at different values of the rectangular transverse coordinate) or many en-face OCT images at many depth positions. Different strategies of scanning are possible as shown in FIG. 3.

OCT has evolved mainly towards producing longitudinal images. Conventional OCT longitudinal scanning uses the strategy in FIG. 3, top, to produce longitudinal OCT images. FIG. 3, middle, shows the strategy used in the en-face scanning to produce longitudinal OCT images. FIG. 3, bottom, shows the strategy used in the en-face scanning to produce en-face images at constant depth. Irrespective of the strategy, the line in the image produced corresponds to the fastest movement. Therefore, in the longitudinal OCT with axial scanning, the line corresponds to the depth, z, and the frame to x, y or θ coordinate. In FIG. 3 top and middle, the example refers to longitudinal images produced in the plane (z,x) and where to cover the volume, the scanning is repeated at different values Y for the coordinate y.

Figure 3:
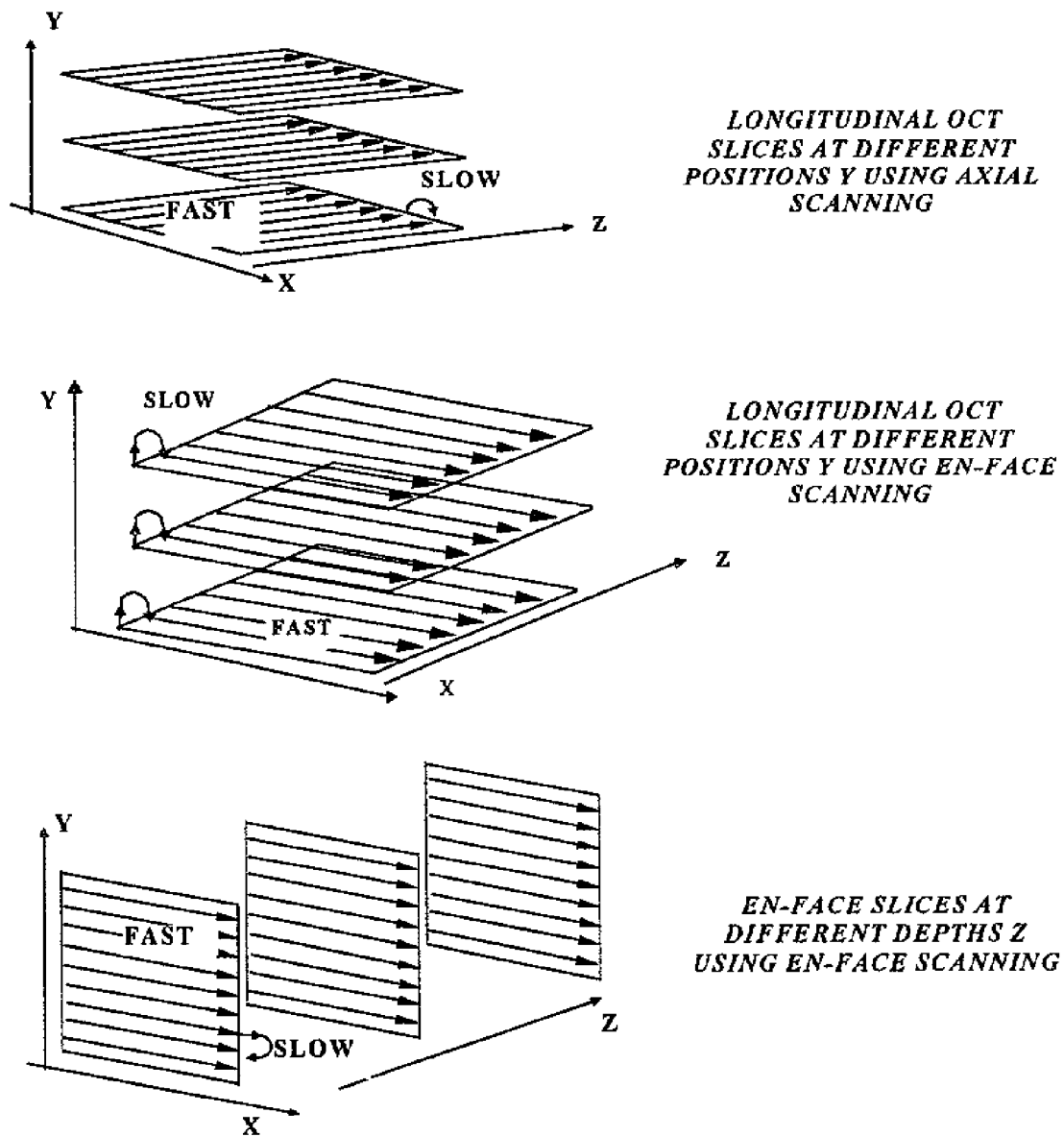
FIG. 3 displays the possible ways of scanning the volume of an object, using either longitudinal OCT imaging (top) or en-face OCT imaging (middle and bottom)

When producing en-face OCT images at constant depth, the line in the raster corresponds to en-face scanning, which in FIG. 3 bottom is along the X direction. The OCT image is produced in the plane (x,y) and to cover the volume, many en-face images are collected at different depths values Z for the coordinate z. In principle it should be equivalent to build the 3D profile from either longitudinal slices or en-face slices as described in the paper: A. Gh. Podoleanu, J. A. Rogers, D. A. Jackson, S. Dunne "Three dimensional OCT images from retina and skin" *Opt. Express*. Vol. 7, No. 9, p. 292–298, (2000), http://www.opticsexpress.org/framestocv7n9.htm. For the same voxel volume (resolution) and number of voxels, the time taken and the amount of memory required for storage is the same irrespective of the method.

Irrespective of the method, the axial eye movements between frames presents an important distortion factor.

Figure 4A:
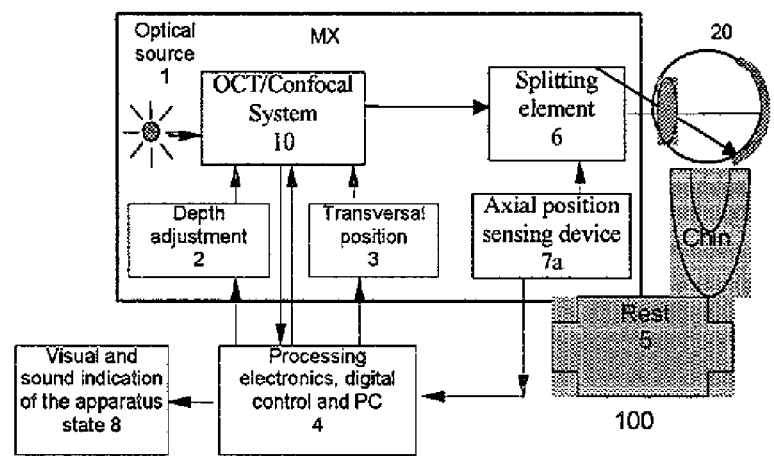
FIG. 4a shows in diagramatic form the embodiment of the system for high resolution imaging of moving organs according to the invention.
Figure 4B:
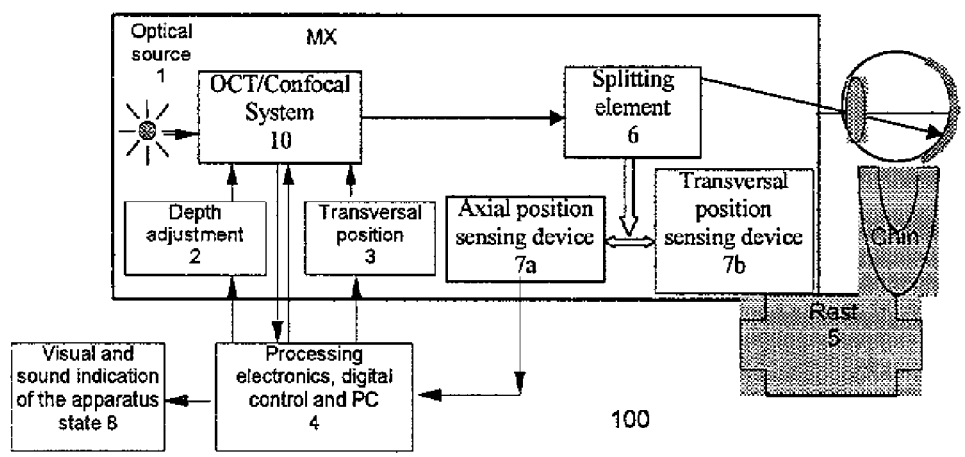
FIG. 4b is similar to FIG. 4a, but shows the presence of both an axial position sensing device and a transverse position sensing device.

FIG. 4a shows, in diagrammatic form, a first embodiment of an (ophthalmic) apparatus 100 in accordance with the present invention. As shown in FIGS. 4a and 4b, the apparatus 100 comprises in addition to the elements in FIG. 2, a splitting element, 6, which allows the common axis of the light to the eye to be shared by the OCT or the OCT/confocal system, 10, and the axial position sensing block, 7a. The axial position of the organ (cornea in the case of the eye) is read by the block 7 and fed into the processing electronics and digital control system, 4. The apparatus according to the invention is also equipped with processing procedures to acquire stacks of images stored in the memory of the control system, 4. A block for error indication 8, informs the user using visual and audio stimuli about the state of the system while acquiring slices under the control of the block 4.

FIG. 4b is similar to FIG. 4a, except that it also shows a second transverse position sensing device 7b. In this case, the splitting element 6 is shared by the interface optics and each of the first and second sensing blocks 7a, 7b. Thus, the interface optics and the first and second sensing blocks have a common axis of the light being transmitted to the object 20 from the light source 1.

Several embodiments of the present invention relate to construction of a stack of en-face OCT images acquired at different depths. This procedure operates in three steps, with the OCT or the OCT/confocal system under the control of the block 4 The block 7a continuously delivers the axial position of the object. At the start of depth scanning, the block 7a is reset. The control block 4 triggers the acquisition of N slices from the depth range $\Delta z = N \delta z$ in a total time intervals $\Delta t = N \delta t$, with δt the time interval between successive frames. Slice n is expected to arrive at the moment $t_n = n \delta t$. The set depth position in the OCT channel is $D_n$. If the eye moves by the error B, the slice is collected from an actual depth position $d_n = D_n - E$.

Figure 5:
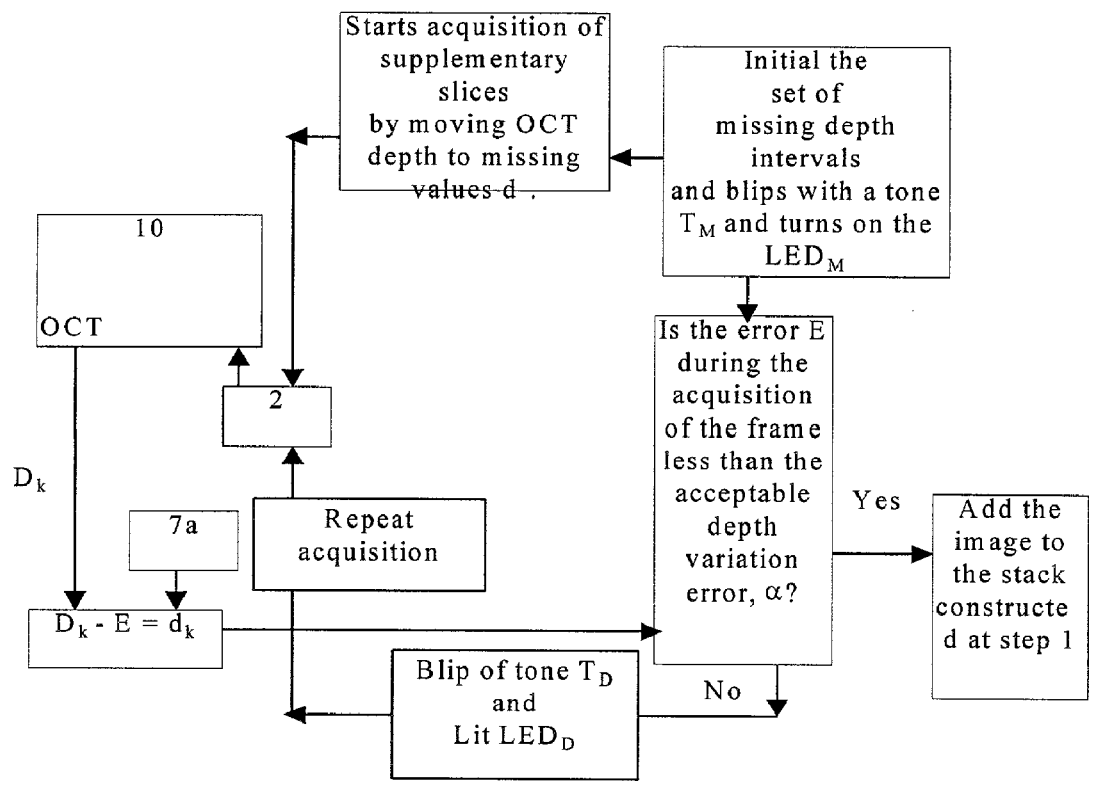
FIG. 5 shows a first flow chart for a method of high resolution imaging of moving organs, to control the acquisition of slices from the missing depth intervals.

According to the four scenarios mentioned above in connection with FIG. 1, the software controls the apparatus to perform three main processing steps, with the $2^{nd}$ and $3^{rd}$ step shown in the flow chart in FIG. 5.

In the first step, the apparatus acquires a stack of en-face images at different depths covering a depth interval, usually the depths being equidistantly separated by an increment δz. At the end of stack collection, using the information supplied by the block of axial position 7a, the apparatus software provides the depth intervals not sampled, $\{d_{miss}\}$. This set also includes the depth intervals where during the acquisition of the frame, the actual depth position varied by more than an acceptable depth variation, $\alpha$. The acceptable value of depth variation is set by the user, usually comparable with the coherence length of the optical source used and as a trade-off between measurement time and depth resolution in the final 3D reconstruction. Any time the organ moved by more than the acceptable depth variation, $\alpha$, the block 8 of the apparatus blips with a tone $T_D$ and an $LED_D$ flashes once.

In a second step of the data acquisition, the system collects en-face OCT images for the missing depth values $\{d_{miss}\}$. To this effect, the optical path in the OCT is tuned automatically to the missing depth value while the block 7a senses the organ position. The depth is corrected by block 7a and block 2 until a slice or more are collected from the missed depth interval $\{d_{miss}\}$. The start of the step 2 is indicated by a blip of tone $T_M$ and optically by an $LED_M$.

A complete stack is formed by putting together the slices collected at step 1 and one slice for each missing interval collected at the step 2. It is also possible that due to the oversampling explained in FIG. 1, several slices, P, are collected at the steps 1 or 2, in which case the software may operate in two possible ways: either only one slice is allocated to the respective depth interval, or the slices are introduced in the complete stack with a weighting factor of 1/P. Using the stack so composed, the 3D volume of the object is subsequently constructed.

In keeping with one embodiment of the invention, the confocal channel is used for validation of those slices in the stack which have shown transverse movements less than a transverse error threshold $\epsilon$. The slices are eliminated in the step 1 and their depths are introduced into the collection of missing depth intervals $\{d_{miss}\}$. In detail, the apparatus operates in the following three steps, with the $2^{nd}$ and $3^{rd}$ step shown in the flow chart in FIG. 6

In the first step, the apparatus acquires a stack of en-face images at different depths covering a depth interval, usually the depths being equidistantly separated by an increment $\delta z$. At the end of stack collection, using the information supplied by the block of axial position 7a, the apparatus software provides the depth intervals not sampled, $\{d_{miss}\}$, which includes the depth intervals where during the acquisition of the frame, the actual depth position varied by more than the acceptable depth variation, $\alpha$. Additionally, slices which have moved transversally by more than a threshold $\epsilon$ are eliminated and their depths recorded in the list of depth intervals not sampled, $\{d_{miss}\}$.

Similarly, the threshold for the acceptable transverse movement, $\epsilon$, is set by the user, comparable with the transverse resolution in the image and as a trade-off between measurement time and transverse resolution in the final 3D reconstruction. Any time the organ moved by more than the acceptable depth variation, $\alpha$, the apparatus blips with a tone $T_D$ and an $LED_D$ flashes once. Any time the organ moved transversally by more than $\epsilon$, the apparatus blips with a tone $T_T$ and a $LED_T$ flashes once.

Figure 6:
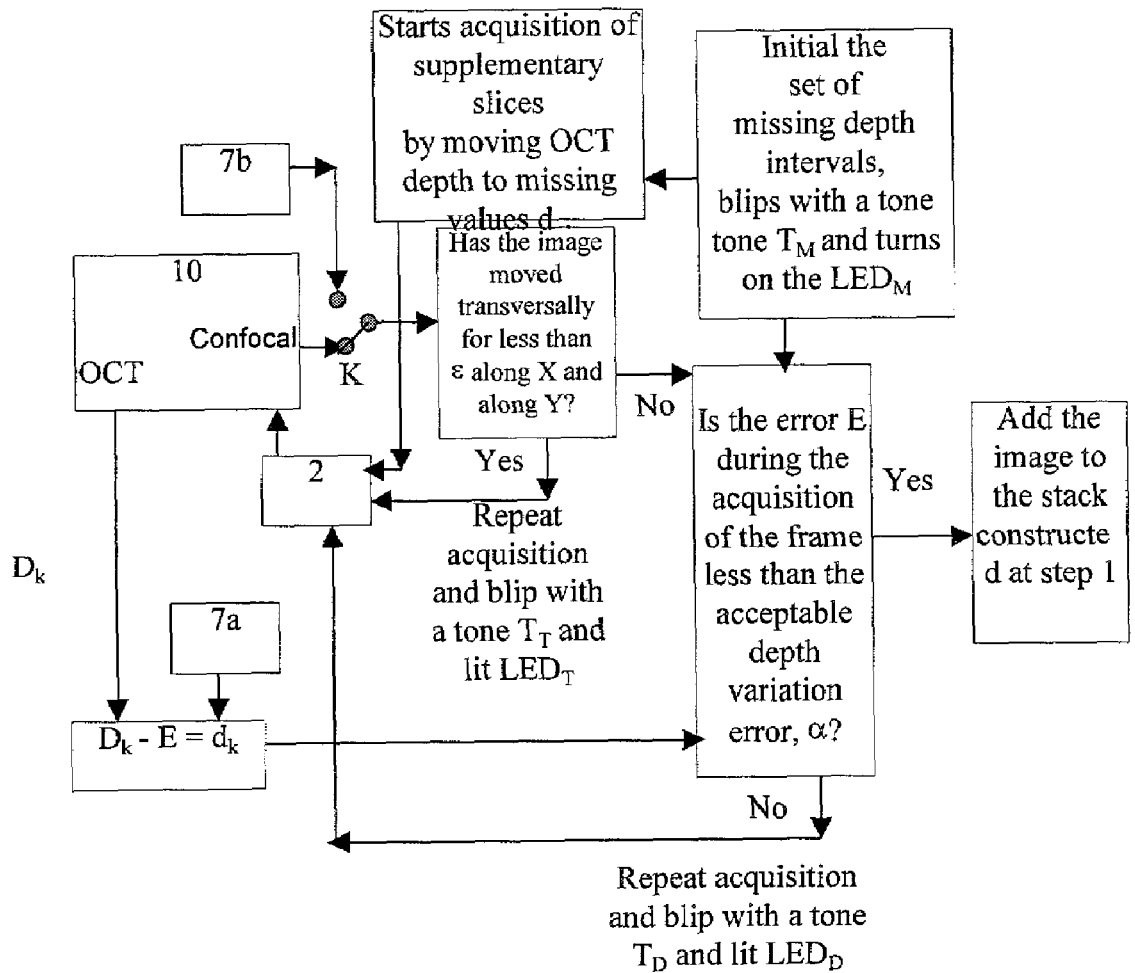
FIG. 6 shows a second flow chart for a method of high resolution imaging of moving organs using en-face OCT, to control the acquisition of slices from the missing depth intervals and evaluate at the same time the transverse position using either the confocal channel or a transverse position sensing device of a dual apparatus, OCT/confocal.

A switch K is provided in the aparatus shown schematically in FIG. 6. This is to allow a choice for the source of the transverse error signal, either from the confocal channel or from the second sensing block.

Also, it should be noted that the two sensing blocks 7a and 7b can operate simultaneously, so as to both validate and infer the axial and transverse shift for subsequent correction.

Here, the transverse movement is evaluated for validation of the frame from either (i), the confocal image after the frame was acquired; or (ii), instantaneously from the values X and Y delivered by the sensing block 7b. In the latter case, the frame can be scrapped before the end of the frame acquisition if a significant movement, larger than the threshold value $\epsilon$, has occurred.

In the transverse alignment of images as described immediately above, the information from either the confocal image in the pair of images, or an average of the values registered by the sensing block 7b during the frame acquisition, is subsequently used.

In a second step of the data acquisition, the system collects en-face OCT images for the missing depth values $\{d_{miss}\}$. To this effect, the optical path in the OCT is tuned automatically to the missing depth value, while the block 7 senses the organ position. The depth is corrected by block 7a and block 2 until a slice or more are collected from the missed depth interval $\{d_{miss}\}$. The start of the step 2 is indicated by a blip of tone $T_M$ and optically by an $LED_M$. During the acquisition, the confocal image continuously validates each new slice for transverse movement less than $\epsilon$. Any time the organ moved transversally by more than $\epsilon$, the apparatus blips with a tone $T_T$ and a $LED_T$ flashes once.

A complete stack is formed by putting together the slices collected at the first step discussed above, and one slice for each missing interval collected at the second step.

It is also possible that due to the oversampling explained in FIG. 1, several slices, P, are collected at the first and second steps discussed above, in which case the software may operate in two possible ways: either only one slice is allocated to the respective depth interval, or the slices are introduced in the complete stack with a weighting factor of 1/P. Using the stack so composed, the 3D volume of the object is subsequently constructed.

Further embodiments of the invention provide apparatus and method for producing 3D volume reconstruction from longitudinal OCT images acquired at different transverse positions selected by the en-face scanning of the organ.

For example the apparatus according to the invention acquires longitudinal OCT images in the plane (x,z), as shown in FIG. 3, top, and middle, for many different values Y of the coordinate y. Due to the axial movements, the entire (x,z) slice collected at $Y_p$ may have moved along z in comparison to the slice (x,z) collected at $Y_{p+1}$. In order to eliminate the effect of the organ movement during the acquisition of the stack of images, the system operates in the following steps, as shown in the flow chart in FIG. 7.

In the first step, the apparatus acquires a stack of longitudinal OCT images at different values of the transverse rectangular coordinate covering a transverse rectangular interval, usually the transverse rectangular positions being equidistantly separated by an increment $\Delta y$. Using the information supplied by the block of axial position 7a, the apparatus discards those images and the associated values, $Y_k$, where during the frame acquisition, the actual depth position varied by more than the acceptable depth variation error, $\alpha$. Any time the organ moves by more than $\alpha$, the apparatus blips with a tone $T_D$ and the $LED_D$ flashes once. The transverse position values of the slices eliminated are provided as a set of missing rectangular transverse coordinates $\{Y_k\}$ as input to the second step described above, using the apparatus of the present invention. Otherwise, if during the frame acquisition, the axial position supplied by the axial sensing block 7a shows variation less than the acceptable depth variation $\alpha$, an average of the depth positions recorded over the frame acquisition time is attached to the slice (x,z), the image is validated and introduced in the stack of images.

Figure 7A:
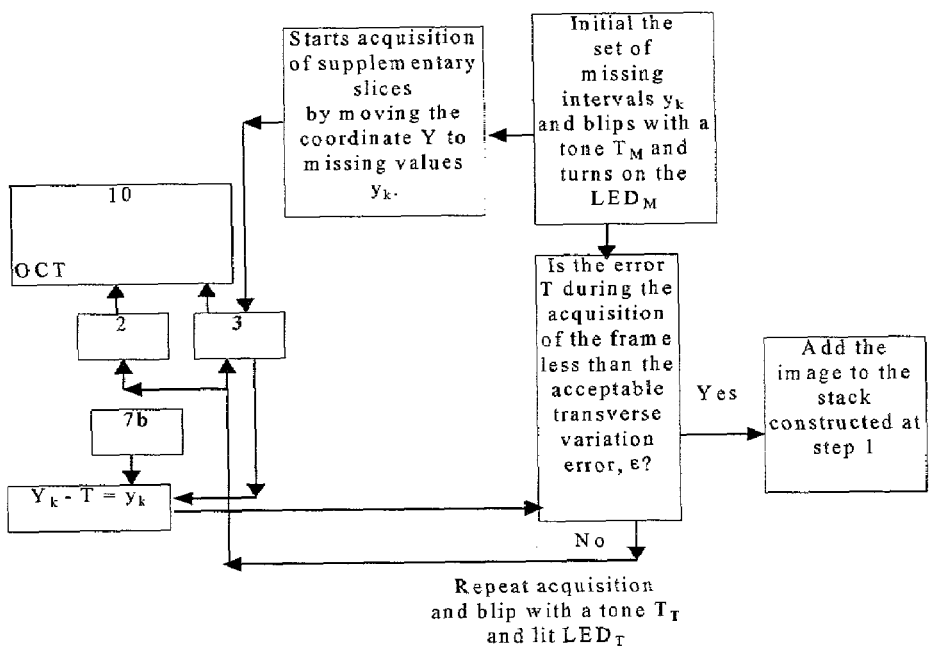
FIG. 7a is a third flow chart for a method of high resolution imaging of moving organs when acquiring longitudinal OCT images, to control the acquisition of slices from the missed transverse coordinate intervals, wherein transverse movement was too large.
Figure 7B:
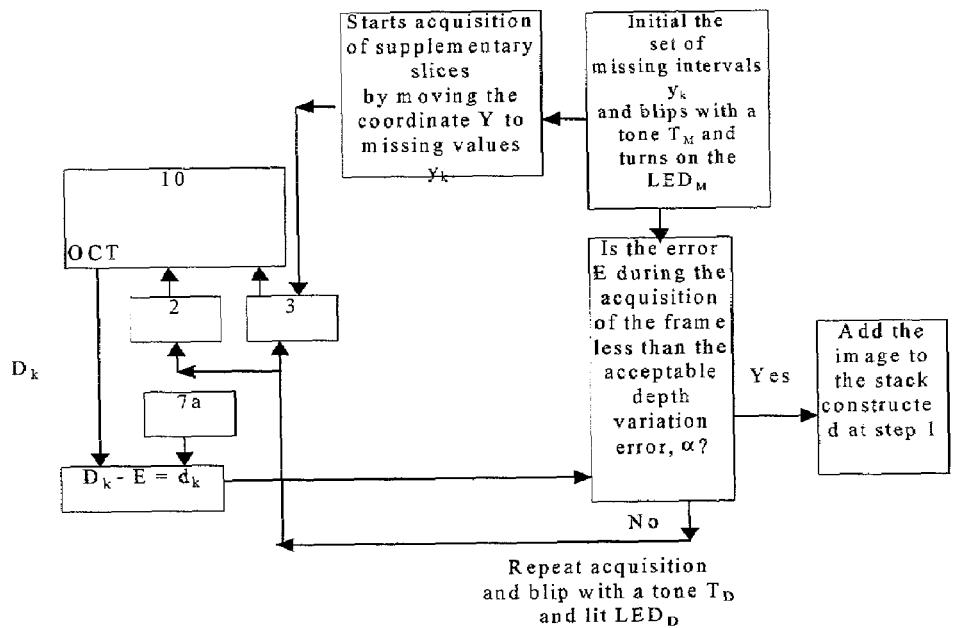
FIG. 7b is a fourth flow chart for a method of high resolution imaging of moving organs using longitudinal OCT, to control the acquisition of slices from the missed transverse coordinate intervals, wherein axial movement was too large.

The apparatus proceeds towards the second step as described in the flow diagram in FIG. 7.

A new acquisition is triggered for the values of the transverse rectangular coordinate in the missing set, $\{Y_k\}$, where the slice collected is validated and added to the set at the first step only if the maximum axial movement of the organ during the slice acquisition is less than the acceptable depth variation, $\alpha$.

Then, the images in the sets of images of the two steps described immediately above are merged into a stack of images which are subsequently aligned according to their attached average depth position, and then used to reconstruct the 3D profile of the object.

In a preferred embodiment of the invention, when longitudinal OCT images are acquired, the confocal channel is used for validation of slices in the stack which have shown transverse movements along the transverse scanning coordinate less than a threshold $\epsilon$, In the example used here, the en-face coordinate is X.

Figure 8:
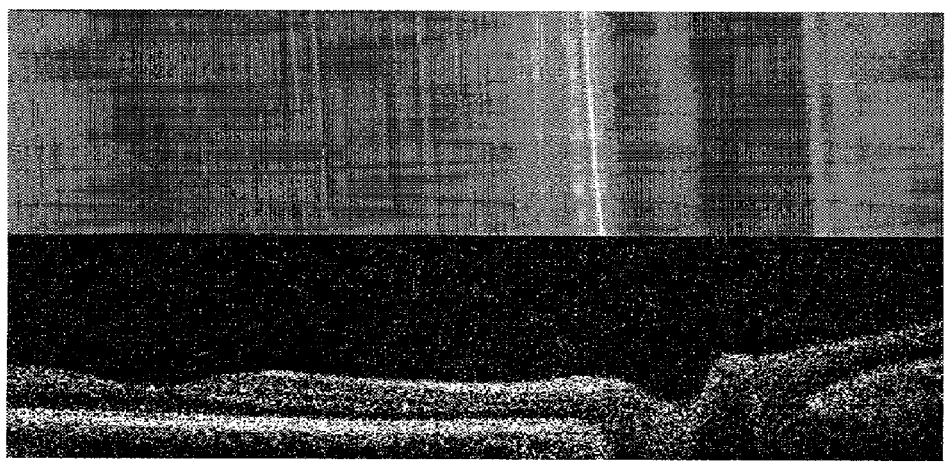
FIG. 8 shows a pair of images acquired with an OCT/confocal standalone system built according to U.S. Pat. No. 5,975,697, wherein the confocal image shows lateral movement of successive horizontal lines along the depth while acquiring the OCT longitudinal image.

An example of a longitudinal image (x,z) collected simultaneously with the confocal image (x) from the retina is shown in FIG. 8. The lateral movement along the scanned direction, X, is obviously seen in the confocal image. During the depth scanning along Z, the eye has moved transversally along X and the amount of movement can easily be inferred from the shift in the shades and lines in the confocal image, otherwise insensitive to depth.

Figure 9A:
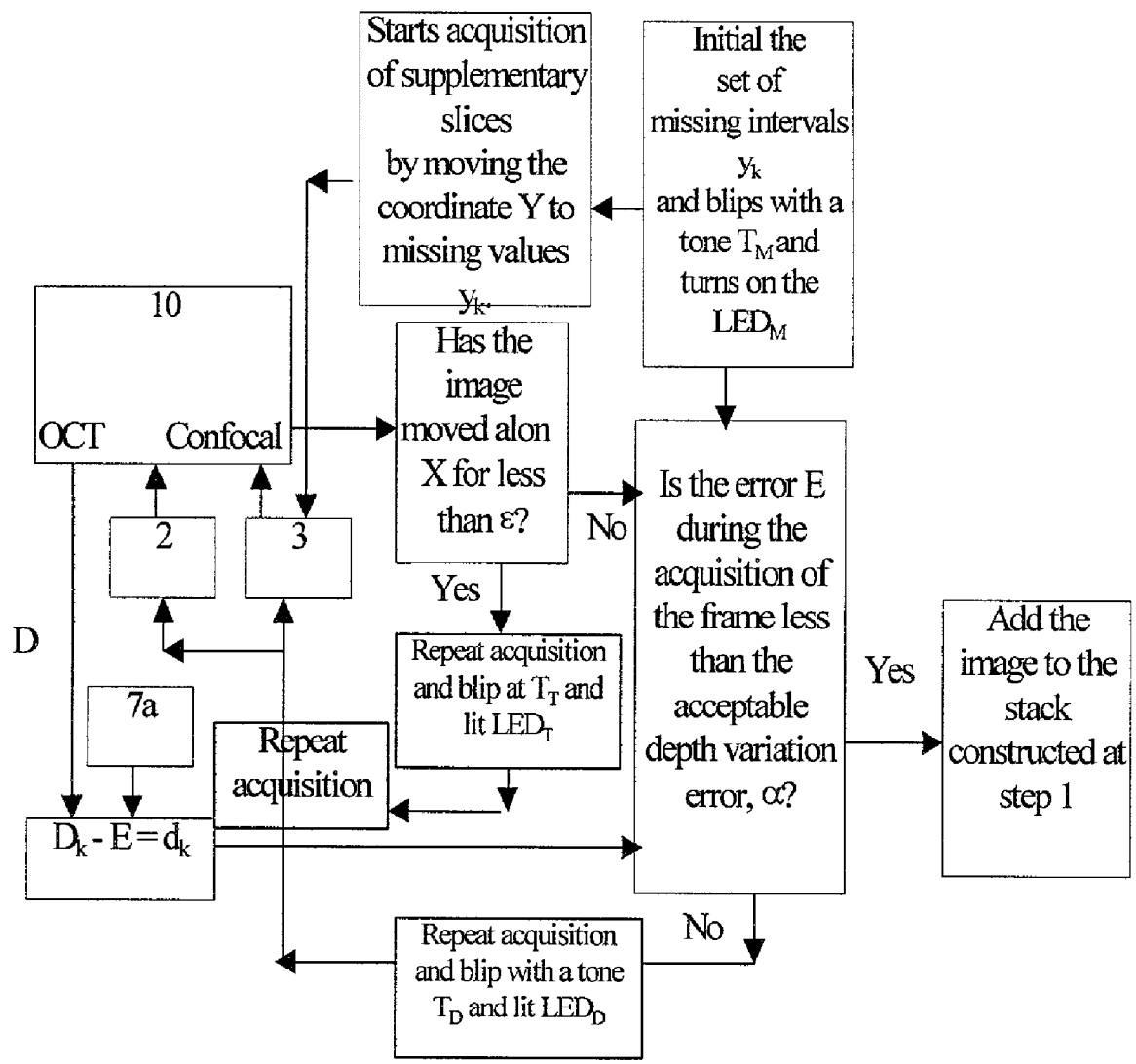
FIG. 9a shows a fifth flow chart for a method of high resolution imaging of moving organs using longitudinal OCT, to control the acquisition of slices from the missing transverse coordinate intervals and to evaluate at the same time the overall transverse coordinate position in the plane of the longitudinal OCT image, using the confocal channel of a dual apparatus, OCT/confocal.

So far the confocal image was used to align the OCT images, as described in U.S. Pat. No. 5,975,697. However, in the present invention, the confocal image employed in real time in the second step as mentioned immediately above, to validate the image collected, according to the flow chart in FIG. 9a. Many such images are acquired until two conditions are satisfied: transverse movement less than threshold $\epsilon$ and axial movement less than the acceptable depth variation, $\alpha$. Therefore, the axial position measurement block 7a needs working at a rate at least 10 times faster than the frame rate. For instance, the frame rate is 1 Hz in a commercial Humphrey™ OCT instrument, and 0.5 Hz in the systems reported in a paper "Three Dimensional OCT Images From Retina and Skin", by A. Gh. Podoleanu, J. A. Rogers, D. A. Jackson, and S. Dunne, reported in *Opt. Express*. Vol. 7, No. 9, pp. 292–298 (2000) and at http://www.opticsexpress.org/framestocv7n9.htm. In that case, the sensing block 7a should provide depth position at the rate of 10 or 20 Hz. Even if the OCT with or without a confocal channel operates at video rate, 20 Hz, the block 7a could still be devised with the actual technology, as 200 Hz operating frequency is quite possible for any of the uses of the present apparatus as proposed in the present application. The flow chart may also include, as shown in FIG. 9a, a validation loop for the axial movements working similarly to the procedure described in connection to FIGS. 5, 6 and 7 above.

Figure 9B:
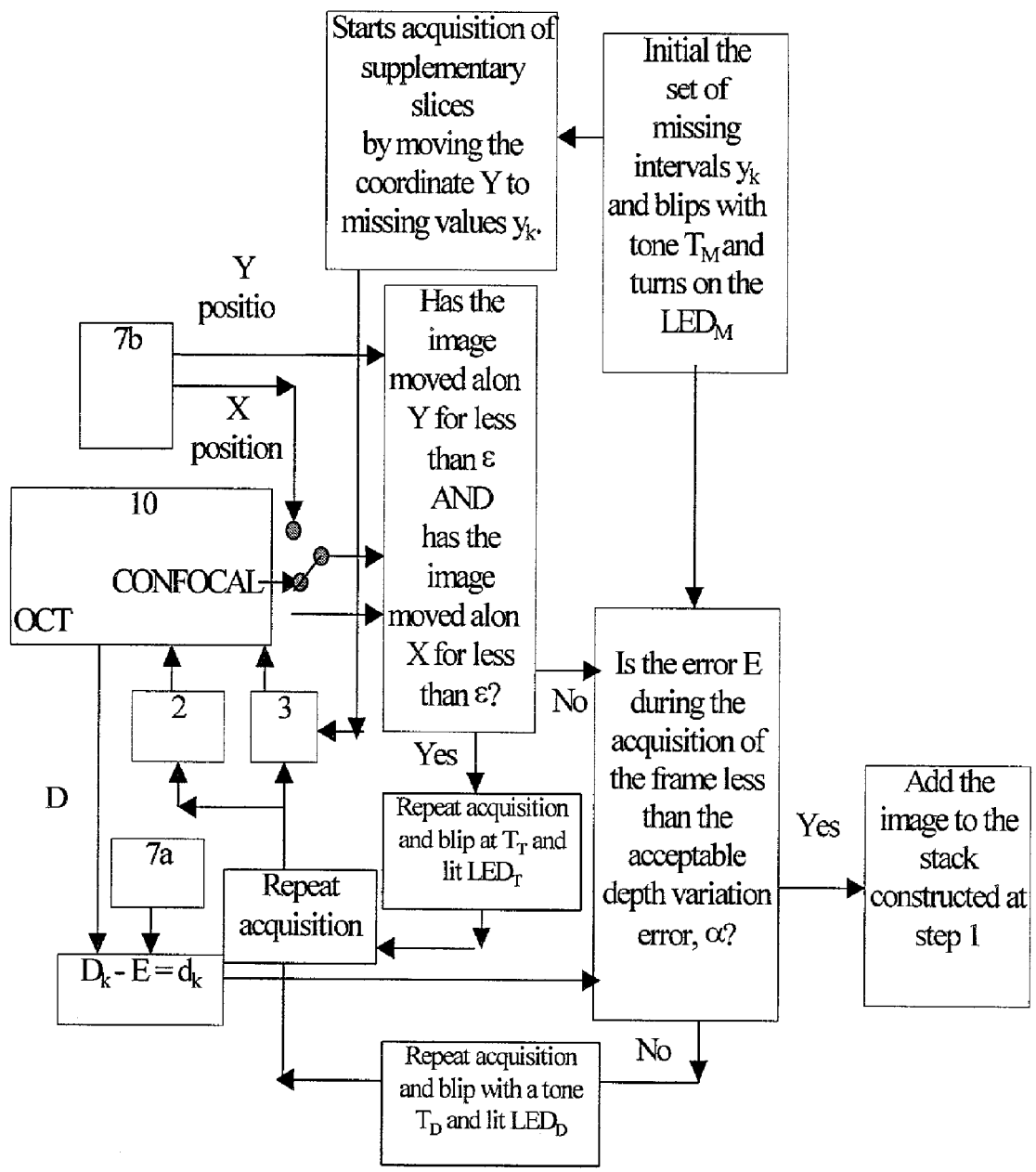
FIG. 9b shows a sixth flow chart for a method of high resolution imaging of moving organs using longitudinal OCT, to control the acquisition of slices from the missing transverse coordinate intervals and to evaluate at the same time the overall transverse position (i) along the transverse coordinate in the plane of the longitudinal OCT image, using either the confocal channel or the signal error delivered by the transverse position sensing device, of a dual apparatus, OCT/confocal; and (ii), along the transverse coordinate rectangular to the plane of the longitudinal OCT image, using the signal error delivered by the transverse coordinate sensing device.

Referring briefly to FIG. 9b, the switch K is employed for the same reasons described above. Also, it will be noted that apparatus as schematically proposed in FIG. 9b employs both a first axial sensing block 7a and a transverse coordinate position sensing block 7b.

FIG. 9b shows a further embodiment, in schematic manner, of the use of apparatus in keeping with the present invention to generate longitudinal OCT images, wherein the acquisition of slices from the missing transverse coordinate intervals is controlled and at the same time the overall transverse position is evaluated (i) along the transverse coordinate in the plane of the longitudinal OCT image, using either the confocal channel or the signal error delivered by the transverse position sensing device, of a dual apparatus, OCT/confocal imaging instrument; and (ii), along the transverse coordinate rectangular to the plane of the longitudinal OCT image, using the signal error delivered by the transverse coordinate sensing device. The flow chart may also include, as shown in FIG. 9b, a validation loop for the axial movements, working similarly to the procedure described in connection to FIGS. 5, 6 and 7 above.

When evaluating the transverse shifts working along the transverse coordinate in the plane of the longitudinal OCT image using the confocal channel, and along the transverse coordinate rectangular to the plane of the longitudinal OCT image using the signal error delivered by the transverse coordinate sensing block 7b, the- sensing device may therefore have only half the number of components otherwise expected to be present.

Movements along X are monitored by the confocal channel 10 and the sensing block 7b, and could also be arranged for sensing shifts along Y only as delivered by the sensing block, 7b.

It is obvious to those skilled in the art that the examples above could be generalised for the case of longitudinal images (y,z) collected at different coordinates x as well as to longitudinal OCT images ($\theta$,z) at different $\rho$ values.

It is also obvious to those skilled in the art that the thresholds for transverse error, $\epsilon$, and the error for depth error, $\alpha$, in the procedures described above can be adjusted by the user as a trade-off between accuracy and total acquisition time for a complete stack.

Figure 10:
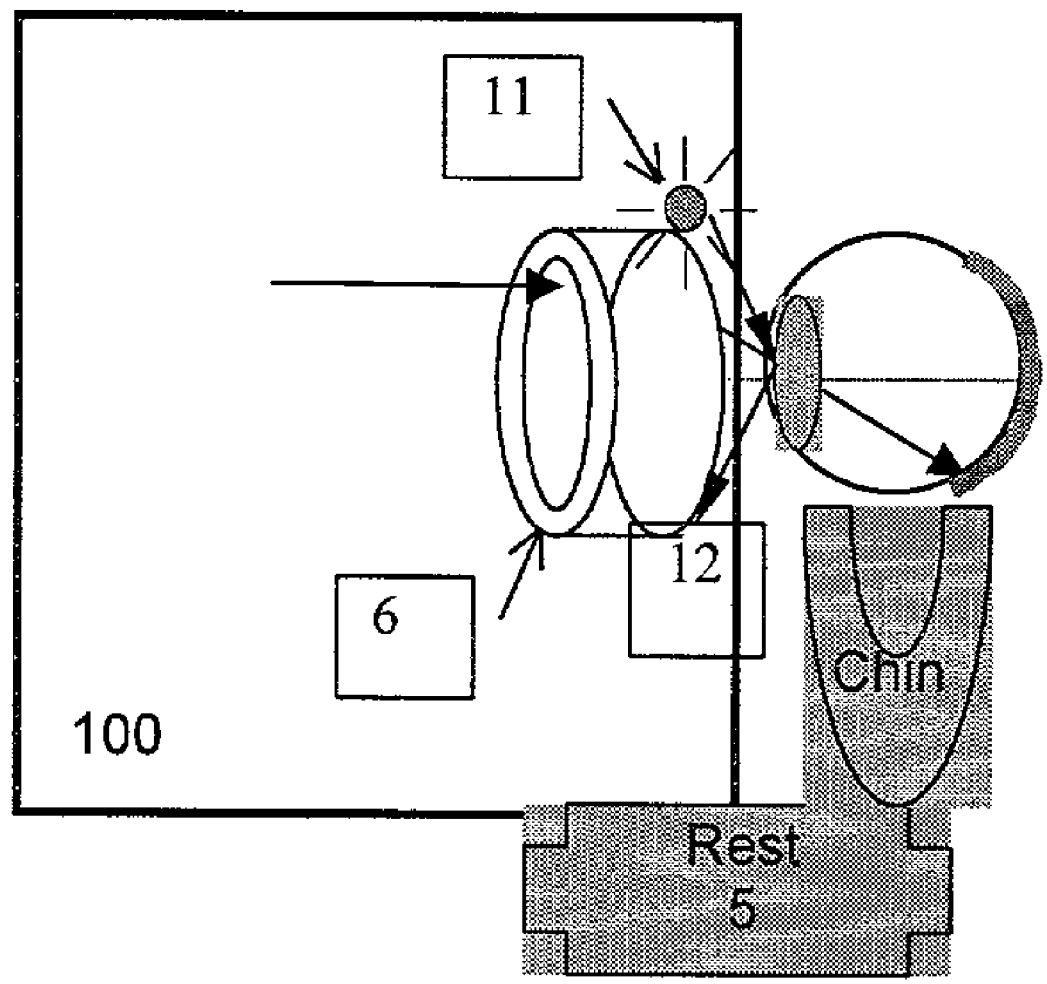
FIG. 10 shows a first configuration for the sensing block of the axial position of the object for the apparatus of high resolution imaging of moving organs, which does not interfere with the imaging beam of the apparatus.

FIG. 10 shows a first embodiment of the sensing block of the axial position using triangulation or other off-axis methods. The triangulation is based on devices and methods known to those skilled in the art, as for instance described in the U.S. Pat. No. 5,028,949. Other off-axis methods may involve pairs of emitters and receivers such as used in the U.S. Pat. No. 6,220,706 or photodetector arrays as described in the U.S. Pat. No. 6,283,954. In keeping with the present invention, however, the splitting element 6 allows complete passage for the OCT beam, or of the OCT/confocal beam, and holds emitters 11 which send beams towards the object, the reflections being collected by detectors 12. Thus the emitters and detectors are outside the system axis, and consequently no optical loss is added to the OCT. Triangulation or other off-axis methods may achieve 50 µm accuracy while operating at kHz rate.

Figure 11:
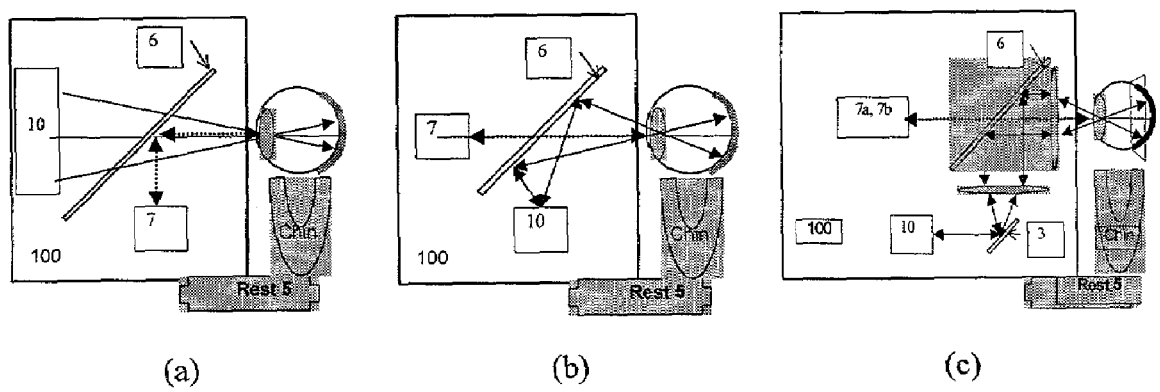
FIG. 11 shows a second configuration for the sensing block of the axial position of the object for the apparatus of high resolution imaging of moving organs, using a beam-splitter, a cold mirror, or a hot mirror.

FIGS. 11a,b,c show a second embodiment of the splitting element where the OCT beam and the beam of the sensing block of the axial—and eventually of the transverse— position 7a and 7b, respectively, share a beam-splitter, 6. If the sensing block of the axial position, 7a, uses optical waves of similar wavelength with that of OCT, then the beam-splitter ratio is chosen as such as the transmission of the OCT signal (when working in transmission) or the reflection of the OCT signal (when working in reflection) to be as high as possible. The beam-splitter 6 can be a cold mirror, a hot mirror, or and edge filter, which is used to transmit wavelengths from one band and reflect wavelengths from a different band. When the beam-splitter 6 is a cold mirror, this may be used for instance to transmit wavelengths larger than 1000 nm, a band used by the OCT/confocal imaging system, 10, and reflects wavelengths smaller than 1000 nm, in a band used by the sensing blocks 7a and 7b. This case is illustrated in FIG. 11a.

FIG. 11b shows the opposite case, where the OCT/confocal system works in reflection and the block 7a and eventually 7b in transmission, using a hot mirror. The hot mirror for instance may be chosen to transmit wavelengths smaller than 1000 nm, a band used by the sensing blocks 7a and 7b, and reflects wavelengths larger than 1000 nm, in a band used by the OCT/confocal imaging system, 10. The utilisation of the beam-splitter 6 in reflection by the imaging system is preferred, as the depth sampling profile of the OCT system is not altered by the dispersion properties of the beam-splitter material.

As is obvious to those skilled in the art, compensation for dispersion can be achieved by the utilization of the same elements of suitable thickness in the reference arm of the interferometer, which results in the best depth resolution interval, up to the level allowed by the line-width of the optical source used.

It is also obvious to those skilled in the art that once the splitting element 6 is in place, different optical methods can be used to sense the position of the object based on the on-axis strong reflection from the object. Such methods could employ principles from RADAR, where the position of the object/organ 20 is temporally coded. Another method could employ frequency modulation of the optical launching radiation emitted by the axial position sensing device, 7a, a method which is known as frequency modulation continuous wave (FMCW), as decribed in "Range finding and velocimetry with directional discrimination using a modulated laser diode Michelson interferometer" By A. Chebbour, C. Gorecki, G. Tribillion, published in *Optics Communication,* 111, (1994), pp 1–5. Alternatively, another OCT system could be used to fast sample the axial position of the object/organ 20, as described in the paper "Fiberised Set-up for Eye Length Measurement", published by A. Gh. Podoleanu, G. M. Dobre, D. J. Webb, D. A. Jackson in *Optics Commun.,* 137, pp. 397–405, (1997). For instance, the OCT/confocal imaging part, 10, of the apparatus according to the invention could operate in the 700–900 nm band and the axial position sensing device, 7a, could employ an OCT system working in the 1100–1500 nm band, which penetrates less in organs having a high water content due to the higher water absorption, but can successfully be used in tracking the axial position of the surface separating the organ from air, such as the cornea when the object is the eye.

The foregoing description has been presented for the sake of illustration and description only. As such, it is not intended to be exhaustive or to limit the invention to any precise form disclosed. For example, modifications and variations are possible in light of the above teaching which are considered to be within the scope of the present invention. Thus, it is to be understood that the claims appended hereto are intended to cover all such modifications and variations which fall within the true scope of the invention.

Throughout this specification and the claims which follow, unless the context requires otherwise, the word "comprise" and variations such as "comprises" or "comprising", will be understood to imply the inclusion of a stated integer or step or group of integers or steps but not to the exclusion of any other integer or step or group of integers or steps.

What is claimed is:

1. Apparatus for high resolution imaging of an object located at an object location and subject to movement during imaging, comprising:
   a) an imaging instrument employing optical coherence tomography (OCT) for scanning said object with an optical sample beam, said imaging instrument including:
      (i) a source of low coherent light;
      (ii) an interferometer for receiving light from said source and outputting said optical sample beam, said interferometer including a first optical path for said optical sample beam and a second optical path for a reference beam;
      (iii) a transverse scanner to effect transverse scanning of the object with said optical beam;
      (iv) depth adjustment means comprising electronically controllable optical path altering means for altering the optical path difference between said first and second optical paths in said interferometer so as to obtain imaging information different axial depth positions relative to said imaging instrument; and
      (v) interface optics for transferring said optical sample beam from the transverse scanner to said object and for transferring said sample beam reflected and scattered from said object back to said interferometer;
   b) a first sensor for sensing the axial position of said object relative to said imaging instrument independently of said imaging instrument so as to detect movement of said object relative to said imaging instrument; and
   c) a processor for acquiring with said imaging instrument a stack of sectional en-face OCT images of said object at different axial depths within said object obtained by altering the optical path difference in said interferometer, said processor being programmed to reject any sectional images for which the movement of said object during the scanning thereof falls outside predetermined acceptable limits in response to a signal from said first sensor.

2. The apparatus of claim 1, wherein said first sensor is chosen from the group consisting of independent low coherence interferometers, and frequency modulation continuous wave devices.

3. The apparatus of claim 1, wherein the processor is configured so that a grid of N depth positions is defined by dividing the range of the depth to be scanned by N, and assigning the respective N depth positions accordingly;
   wherein a depth position for each acquired image is compared with its respective real axial position as determined by said first sensing block;
   wherein for each scanned image a calculated axial position is allocated in keeping with the comparison of the real axial position with said grid;
   wherein a determination is made after a set of images has been acquired as to whether any of the N depth intervals has not been sampled or has been oversampled; and
   wherein a scanning procedure is repeated until each of the N depth intervals on said grid has been sampled at least once.

4. The apparatus of claim 3, wherein the calculated axial position for each slice of a set of images is an average value determined from the axial positions measured by said first sensing block during the acquisition of that slice, and wherein each such calculated axial position is valid or determined only when all axial positions measured by said first sensing block are less than a predetermined threshold axial error.

5. The apparatus of claim 3, wherein the calculated axial position for each slice is the value from said grid of depth values closest to an average depth as determined by said first sensing block during the acquisition of that slice;
   wherein each such calculated axial position is valid or determined only when all axial positions measured by said first sensing block are less than a predetermined threshold axial error; and wherein for more than one image per depth interval collected, the image having a calculated axial position which is closest to the respective grid value is the one which is chosen.

6. The apparatus of claim 3, wherein after a set of images is acquired and a determination is made as to which of the N depth intervals has not been sampled, new slices are collected for each of the depth intervals not yet sampled until each of the N depth intervals on said grid has been sampled at least once; and wherein after a stack of N images with at least one image for each of said N depth intervals has been acquired, a 3D reconstruction of said object is made.

7. The apparatus of claim 3, wherein after a set of images is acquired and a determination is made as to which of the N depth intervals has not been sampled, new slices are collected for each of the depth intervals not yet sampled until each of the N depth intervals on said grid has been sampled at least once;

wherein after at least one image for each of said N depth intervals has been acquired, and where there are P images for any specific depth interval, then each image for each respective depth interval is assigned a weight of 1/P; and wherein after a stack of N images with at least one image for each of said N depth intervals has been acquired, a 3D reconstruction of said object is made.

8. The apparatus of claim 3, wherein said imaging instrument is a dual channel optical coherence tomography/confocal imaging instrument;

wherein a predetermined axial threshold error value is established;

wherein each slice for each depth interval is validated for axial shifts less than the axial threshold error value;

wherein, when a depth interval shift as measured by the first sensing block during the acquisition of the slice is greater than the predetermined axial threshold error value, the scanned slice is discarded and the corresponding depth value is determined not to have been sampled; and wherein the sampling continues until at least one slice has been acquired for each one of said N depth intervals.

9. The apparatus of claim 3, wherein said imaging instrument is a dual channel optical coherence tomography/confocal imaging instrument;

wherein a predetermined axial threshold error value is established;

wherein a predetermined transverse threshold error value is established;

wherein each slice for each depth interval is validated for axial shift less than the axial threshold error value and is also validated, for transverse shifts along any transverse directions, less than the transverse threshold error value;

wherein, when at least one of a depth interval shift as measured by the first sensing block during the acquisition of the slice, and the transverse interval shift along any transverse direction, as measured by the second sensing block during the slice acquisition is greater than the respective predetermined axial threshold error value or the predetermined transverse error threshold value, then the scanned slice is discarded and the corresponding transverse coordinate value is determined not to have been sampled; and wherein the sampling continues until at least one slice has been acquired for each one of said N depth intervals.

10. The apparatus of claim 3, wherein said imaging instrument is a dual channel optical coherence tomography/confocal imaging instrument;

wherein a predetermined axial threshold error value is established;

wherein a predetermined transverse threshold error value is established;

wherein each slice for each depth interval is validated for axial shift less than the axial threshold error value and is also validated, for transverse shifts along any transverse directions, less than the transverse threshold error value;

wherein, when at least one of a depth interval shift as measured by the first sensing block during the acquisition of the slice, and the transverse interval shift along any transverse direction, as measured from the image of the confocal receiver after the slice was acquired by comparing the transverse shift in relation to the first slice at a first depth position, or in relation to a reference slice at a reference depth positionl, is greater than the respective predetermined axial threshold error value or the predetermined transverse error threshold value, then the scanned slice is discarded and the corresponding depth value is determined not to have been sampled; and wherein the sampling continues until at least one slice has been acquired for each one of said N depth intervals.

11. The apparatus of claim 1, wherein a predetermined threshold axial error is established, and is adjustable as a trade-off between axial resolution and acquisition time; and wherein a predetermined threshold transverse coordinate error is optionally established, and is adjustable as a trade-off between transverse coordinate resolution and acquisition time.

12. The apparatus of claim 1, further comprising a beam splitter shared by said first sensor and said interface optics for directing a portion of the sample beam returned from said object to said first sensor.

13. The apparatus of claim 12, wherein said beam splitter is chosen from the group consisting of cold mirrors, hot mirrors, large band beam splitters, and edge filters, whereby separate wavelength bands are allowed to be transmitted and reflected; and wherein one of two separate wavelength bands is allocated to said optical coherence tomography imaging instrument, and the other of said two separate wavelength bands is allocated to said first sensor.

14. The apparatus of claim 12, wherein said first sensor includes second OCT instrument for independently sensing the axial position of said object by optical coherence tomography.

15. The apparatus of claim 1, further comprising a support element for said first sensor, said support element sharing a common axis with said interface optics, and wherein said first sensor is mounted on said support element in an off-axis relationship with said optical sample beam.

16. The apparatus of claim 15, wherein said first sensor comprises at least an emitter-receiver pair mounted on said support element.

17. The apparatus of claim 1, wherein said processor is configured to acquire replacement sectional (OCT) images for any rejected sectional images and to add said replacement sectional (OCT) images to said stack.

18. The apparatus of claim 17, further comprising timing means for establishing a timing reference for said sectional images, and for establishing timing intervals and reference times for said sectional images.

19. The apparatus of claim 1, further comprising a confocal receiver for creating a confocal sectional image associated with each said sectional OCT image, said imaging instrument being a dual channel optical coherence tomography/confocal imaging instrument.

20. Apparatus for high resolution imaging of an object located at an object location and subject to movement during imaging, comprising:
   a) an imaging instrument employing optical coherence tomography (OCT) for scanning said object with an optical sample beam, said imaging instrument including:
      (i) a source of low coherent light;
      (ii) an interferometer for receiving light from said source and outputting said optical sample beam, said interferometer including a first optical path for said optical sample beam and a second optical path for a reference beam;
      (iii) depth adjustment means comprising electronically controllable optical path altering means for altering the optical path difference between said first and second optical paths in said interferometer so as to obtain imaging information at different axial depth positions relative to said imaging instrument;
      (iv) transverse coordinate adjustment means comprising electronically controllable optical path altering means for altering the rectangular transverse coordinate along an axis which is orthogonal to a transverse scanning axis to permit a series of sectional OCT longitudinal images of the object to be obtained; and
      (v) interface optics for transferring said optical sample beam from the transverse scanner to said object and for transferring said sample beam reflected and scattered from said object back to said interferometer;
   b) a first sensor for sensing the axial position of said object independently of said OCT imaging instrument;
   c) a second sensor for sensing the transverse position of said object independently of said OCT imaging instrument; and
   d) a processor for acquiring with said imaging instrument a stack of said sectional longitudinal OCT images of said object said processor being programmed to reject any sectional images for which the movement of said object during the scanning of said images falls outside predetermined acceptable limits in response to signals from said first and second sensors.

21. The apparatus of claim 20, wherein said first and second sensors each employ at least an emitter-receiver pair mounted on a support element configured so as to provide axial and transverse coordinate position information for the object respectively.

22. The apparatus of claim 20, wherein at least one of said first sensor and said second sensor is chosen from the group consisting of independent low coherence interferometers, and frequency modulation continuous wave devices.

23. The apparatus of claim 20,
   wherein the processor is configured so that a grid of N transverse coordinate positions is defined by dividing the range of the transverse coordinate to be scanned by N, and assigning the respective N transverse coordinate positions accordingly;
   wherein a transverse coordinate position for each acquired image is compared with its respective real transverse position as determined by said second sensing block;
   wherein for each scanned image a calculated transverse coordinate position is allocated in keeping with the comparison of the real transverse position with said grid;
   wherein a determination is made after a set of images has been acquired as to whether any of the N transverse coordinate intervals has not been sampled or has been oversampled; and
   wherein a scanning procedure is repeated until each of the N transverse coordinate intervals on said grid has been sampled at least once.

24. The apparatus of claim 23, wherein the calculated transverse coordinate position for each slice of a set of images is an average value determined from the transverse coordinate positions measured by said second sensing block during the acquisition of that slice, and wherein each such calculated transverse coordinate position is valid or determined only when all transverse coordinate positions measured by said second sensing block are less than a predetermined threshold transverse coordinate error.

25. The apparatus of claim 23, wherein the calculated transverse coordinate position for each slice is the value from said grid of transverse coordinate values closest to an average transverse coordinate as determined by said second sensing block during the acquisition of that slice;
   wherein each such calculated transverse coordinate position is valid or determined only when all transverse coordinate positions measured by said second sensing block are less than a predetermined threshold transverse coordinate error; and
   wherein for more than one image per transverse coordinate interval collected, the image having a calculated transverse coordinate position which is closest to the respective grid value is the one which is chosen.

26. The apparatus of claim 23, wherein after a set of images is acquired and a determination is made as to which of the N transverse coordinate intervals has not been sampled, new slices are collected for each of the transverse coordinate intervals not yet sampled until each of the N transverse coordinate intervals on said grid has been sampled at least once; and
   wherein after a stack of N images with at least one image for each of said N transverse coordinate intervals has been acquired, a 3D reconstruction of said object is made.

27. The apparatus of claim 23, wherein after a set of images is acquired and a determination is made as to which of the N transverse coordinate intervals has not been sampled, new slices are collected for each of the transverse coordinate intervals not yet sampled until each of the N transverse coordinate intervals on said grid has been sampled at least once;
   wherein after at least one image for each of said N transverse coordinate intervals has been acquired, and where there are P images for any specific transverse coordinate interval, then each image for each respective transverse coordinate interval is assigned a weight of 1/P; and
   wherein after a stack of N images with at least one image for each of said N transverse coordinate intervals has been acquired, a 3D reconstruction of said object is made.

28. The apparatus of claim 23, wherein said imaging instrument is a dual channel optical coherence tomography/confocal imaging instrument;
   wherein a predetermined transverse threshold error value is established;

wherein each slice is validated for transverse shifts along the transverse scanning direction less than the transverse threshold error value;

wherein, when at least one of the transverse interval shift along any transverse scanning direction as measured by the second sensing block, or one of the transverse interval shifts along the transverse scanning direction as measured from the image of the confocal receiver after the slice was acquired by comparing the transverse shift of lines along depth in relation to a line at a first depth coordinate interval, or in relation to a reference line in the image at a reference depth interval, is greater than the transverse threshold error value, then the scanned slice is discarded and the corresponding transverse coordinate value is determined not to have been sampled; and wherein the sampling continues until at least one slice has been acquired for each one of said N transverse coordinate intervals.

29. The apparatus of claim 20, wherein said imaging instrument is a dual channel optical coherence tomography/confocal imaging instrument;

wherein a predetermined axial threshold error value is established;

wherein a predetermined transverse threshold error value is established;

wherein each slice for each depth interval is validated for axial and transverse shifts less than the axial threshold error value and the transverse threshold error value respectively;

wherein, when at least one of a depth interval shift as measured by the first sensing block during the acquisition of the slice, and a transverse interval shift as measured by the second sensing block during the acquisition of the slice, is greater than the respective predetermined axial threshold error value or the predetermined transverse threshold error value, then the scanned slice is discarded and the corresponding depth value is determined not to have been sampled; and wherein the sampling continues until at least one slice has been acquired for each one of said N depth intervals.

30. The apparatus of claim 20, wherein a longitudinal optical coherence tomography slice is acquired for each one of a grid of N equidistant transverse coordinate positions that are within the transverse coordinate range; and wherein the calculated transverse position for each one of said N transverse coordinate positions is an average value determined from the transverse coordinate positions measured by said second sensing block during the acquisition of that slice; and wherein each such calculated transverse coordinate position is valid or determined only when all transverse coordinate positions measured by said second sensing block are less than a predetermined threshold transverse coordinate error.

31. The apparatus of claim 30, wherein for each scanned slice, a calculated transverse position is allocated in keeping with a comparison of the respective real transverse position as determined by said second sensing block;

wherein a determination is made after a set of slices has been acquired as to whether any of the N transverse coordinate positions has not been sampled or has been oversampled; and wherein a scanning procedure is repeated until each of the N transverse coordinate positions on said grid has been sampled at least once.

32. The apparatus of claim 31, wherein the calculated transverse coordinate position for each slice is the value from said grid of transverse coordinate values closest to an average transverse coordinate as determined by said second sensing block during the acquisition of that slice;

wherein each such calculated transverse coordinate position is valid or determined only when all transverse coordinate positions measured by said second sensing block are less than a predetermined threshold transverse coordinate error; and wherein for more than one image per transverse coordinate interval collected, the image having a calculated transverse coordinate position which is closest to the respective grid value is the one which is chosen.

33. The apparatus of claim 31, wherein after a set of images is acquired and a determination is made as to which of the N depth intervals has not been sampled, new slices are collected for each of the transverse coordinate intervals not yet sampled until each of the N transverse coordinate intervals on said grid has been sampled at least once; and wherein after a stack of N images with at least one image for each of said N transverse coordinate intervals has been acquired, a 3D reconstruction of said object is made.

34. The apparatus of claim 20, wherein said imaging instrument is a dual channel optical coherence tomography/confocal imaging instrument;

wherein a predetermined axial threshold error value is established;

wherein a predetermined transverse threshold error value is established;

wherein each slice for each depth interval is validated for axial shift less than the axial threshold error value and is also validated for transverse shifts along rectangular transverse directions less than the transverse threshold error value;

wherein, when at least one of a depth interval shift as measured by the first sensing block during the acquisition of the slice, and a transverse interval shift along a rectangular transverse direction to the transverse scanning in the longitudinal OCT image, as measured by the second sensing block during acquisition of the slice, is greater than the respective predetermined axial threshold error value and the predetermined transverse error threshold value; or when a transverse interval shift along the transverse scanning direction as measured from the image of the confocal receiver after the slice was acquired by comparing the transverse shift of lines along depth in the OCT channel in relation to a line at a first depth coordinate interval, or in relation to a reference line in the image at a reference depth interval, is greater than the predetermined transverse error threshold value; then the scanned slice is discarded and the corresponding transverse coordinate value is determined not to have been sampled; and wherein the sampling continues until at least one slice has been acquired for each one of said N transverse coordinate intervals.

35. The apparatus of claim 20, wherein a predetermined threshold transverse coordinate error is established, and is adjustable as a trade-off between transverse coordinate resolution and acquisition time; and wherein a predetermined threshold axial error is optionally established, and is adjustable as a trade-off between axial resolution and acquisition time.

36. The apparatus of claim 20,
wherein a predetermined axial threshold error value is established;
wherein each slice for each depth interval is validated for axial shift less than the axial threshold error value;
wherein, when a depth interval shift as measured by the first sensor during the acquisition of the slice is greater than the predetermined axial threshold error value, the scanned slice is discarded and the corresponding transverse coordinate value is determined not to have been sampled; and
wherein the sampling continues until at least one slice has been acquired for each one of N transverse coordinate intervals.

37. The apparatus of claim 20, wherein said imaging instrument is a dual channel optical coherence tomography/confocal imaging instrument;
wherein a predetermined axial threshold error value is established;
wherein a predetermined transverse threshold error value is established;
wherein each slice for each depth interval is validated for axial shift less than the axial threshold error value and is also validated, for transverse shifts along the transverse scanning direction in the longitudinal OCT image, less than the transverse threshold error value;
wherein, when at least one of a depth interval shift as measured by the first sensing block during the acquisition of the slice, and the transverse interval shift along the transverse scanning direction in the longitudinal OCT image, as measured from the image of the confocal receiver after the slice was acquired by comparing the transverse shift of lines along depth in the OCT channel in relation to a line at a first depth coordinate interval, or in relation to a reference line in the image at a reference depth interval, is greater than the respective predetermined axial threshold error value or the predetermined transverse error threshold value, then the scanned slice is discarded and the corresponding transverse coordinate value is determined not to have been sampled; and
wherein the sampling continues until at least one slice has been acquired for each one of said N transverse coordinate intervals.

38. The apparatus of claim 20, wherein said second sensor is provided by a confocal receiver associated with said OCT imaging instrument to provide a dual channel optical coherence tomography/confocal imaging instrument.

39. The apparatus of claim 20, further comprising a beam splitter shared by said first sensor and said interface optics for directing a portion of the sample beam returned from said object to said first and second sensors.

40. The apparatus of claim 39, wherein said beam splitter is chosen from the group consisting of cold mirrors, hot mirrors, large band beam splitters, and edge filters, whereby separate wavelength bands are allowed to be transmitted and reflected; and
wherein one of two separate wavelength bands is allocated to said optical coherence tomography imaging instrument, and the other of said two separate wavelength bands is allocated to said second sensor.

41. The apparatus of claim 20, wherein said processor is configured to acquire replacement sectional (OCT) images for any rejected sectional images and to add said replacement sectional (OCT) images to said stack.

42. The apparatus of claim 41, further comprising timing means for establishing a timing reference for said sectional images, and for establishing timing intervals and reference times for said sectional images.

* * * * *